US00PP08702P

United States Patent [19]

Gillespie

[11] Patent Number: Plant 8,702

[45] Date of Patent: Apr. 26, 1994

[54] APPLE VARIETY NAMED STARLITE

[76] Inventor: Paul Gillespie, P.O. Box 8612, Havelock North, Hastings, New Zealand

[21] Appl. No.: 945,062

[22] Filed: Sep. 15, 1992

[51] Int. Cl.[5] ..... A01H 5/00

[52] U.S. Cl. ..... Plt.34.1

[58] Field of Search ..... Plt. 34.1

[56] References Cited

PUBLICATIONS

Technical Questionnaire.

Objective Description of Variety.

New Zealand Plant Variety Rights Journal, No. 47, Jul.-Sep. 1991, pp. 5-7 (Oct. 14, 1991).

*Primary Examiner*—James R. Feyrer

*Attorney, Agent, or Firm*—Quarles & Brady

[57] ABSTRACT

The new and distinct variety is a seedling variety of unknown appearance. The new variety is designated "Starlite". The fruit of this variety has an attractive appearance characterised by a high percentage of burgundy-red overcolour.

4 Drawing Sheets

SUMMARY OF THE INVENTION

The present invention relates to a new and distinct apply variety. More particularly the new cultivar is designated 'Starlite' and is a seedling variety of unknown parentage. After the variety was discovered in a former chicken run in the backyard of a private residence on Te Mata, Mangateretere Road, Hastings, New Zealand, it was asexually reproduced in 1985 at Gillespie Orchards, Te Mata, Mangateretere Rd, Hastings, New Zealand by budding onto rootstock of the MM106 variety. The fruit was first observed on the reproduced plants in 1988. It has not been possible to determine the parentage of this variety as it presumably arose from a seed of an apple fed to the chickens occupying the chicken run.

Asexual propagation shows that the unique combination of characteristics and distinctive colour come true to form and are established and transmitted through succeeding propagations.

DESCRIPTION OF THE PHOTOGRAPHS

The invention may be more fully understood by having reference to the accompanying photographic colour reproductions, which show typical specimens of the fruit of the new variety as depicted in colours as nearly true as is reasonably possible to make the same in a colour illustration of this character.

DETAILED DESCRIPTION

Figure 1:
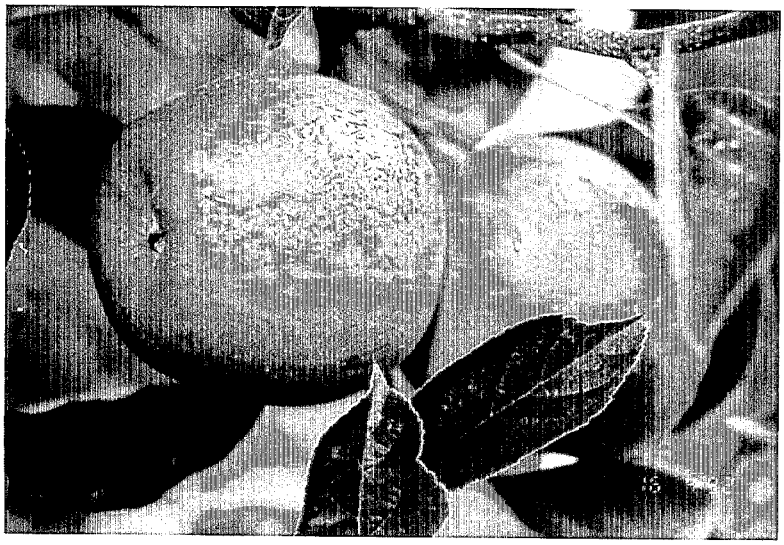
FIG. 1 shows typically specimens of fruit of the variety on the tree.
Figure 2:
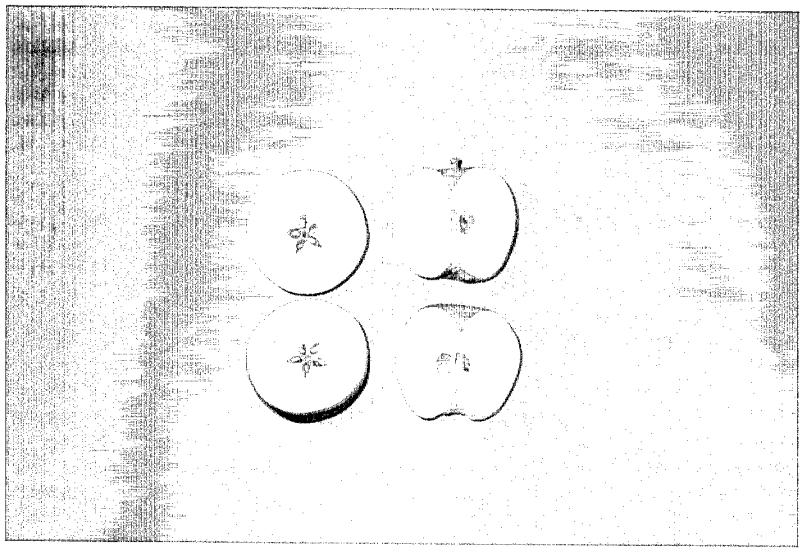
FIG. 2 shows two cross-sectional views of the fruit of Starlite.
Figure 3:
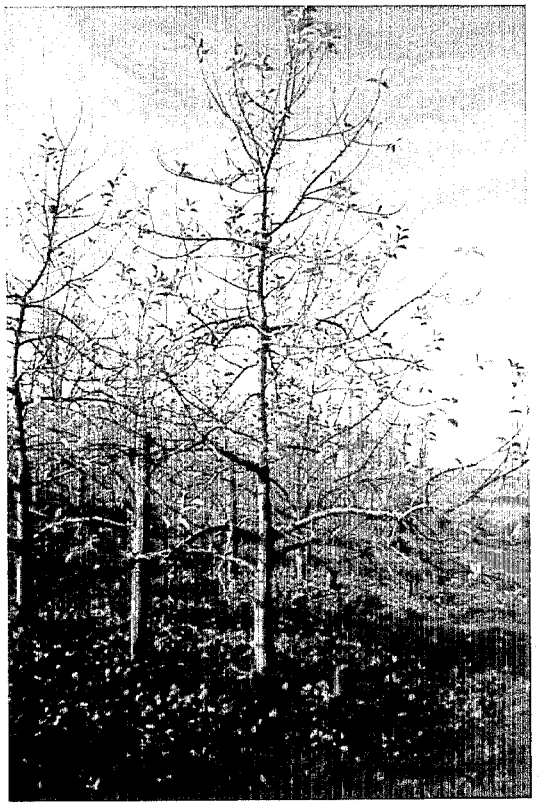
FIG. 3 shows the three of Starlite in the dormant state.
Figure 4:
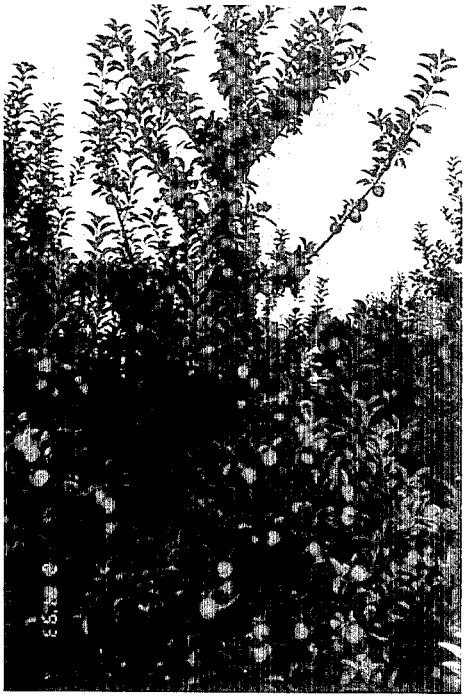
FIG. 4 shows the tree of Starlite with fruit.

The distinctive characteristics of this new apple cultivar described below were observed in Hastings, New Zealand. The trees were 5 to 7 years old at the time. The colour designations hereinafter set forth are according to the Munsell Colour System using a Minolta Colour Meter.

Tree: medium vigour; spreading habit; predominance of bearing on spurs; similar habit and spurring characteristics to Red Delicious "Red Chief"; branches form at an angle 70°-80° to the main trunk; pruning requirements are light; approximate terminal growth of eighteen inches; at seven years after asexual reproduction, the trees have a width of three meters and a heights of four meters; a crop of approximately five bushels per tree is obtained at seven years; fruit thinning is required to obtain fruit of marketable size; the trees will come into bearing in the year following grafting and are annual bearing; the bark is brown Colour 7.5 YR 4/1.

Dormant one year old shoot: (Observed in winter on trees at least years old) weak pubescence on upper half; thick; medium number of lenticels; brown colour on sunny side; medium bud size; pointed bud tip; position of bud relative to axis, adpressed; medium bud support; dormant fruit bud shape (on spurs), conical-ovoid.

Flower: Colour of bud just before flower opens, pink; time of beginning of flowering (10% flowers), pink; time of begining of flowering, late; flowers at approximately the same time as Fuji, entering full bloom between 12 and 16 October at Hastings; (Observation of flowers at start of anther dehiscence) flat or slightly cupped shape; larger size; position of margin of petals, free.

*Pollination.*—Fuji is a suitable pollinator.

Leaf: (Mature leaves observed in summer when they form ⅓ of an upright growing shoot on outside of tree) early bud burst; pose of leaf, upwards; medium leaf size; from 4th to 6th fully expanded leaf, length 83 mm, width 56 mm; length/width ratio of blade, medium; shape in cross section, upfolded; indentation of margin, serrate; medium glossiness of upper side; weak pubescence on lower side, petiole length, 25 mm; small stipule size; colour of leaf underside is green 2.5 GY5/3; colour of leaf upper side is 7.5GY3/1.

Fruit:

*Size.*—Medium-large; length 61 mm, breadth 73 mm.

*Shape.*—Medium truncate; symmetric in side view, weak crowning at distal end.

*Eye.*—Closed; medium size.

*Eye basin.*—Medium depth; medium width; ribbing present.

*Sepals.*—Medium length; touching at base.

*Stalk.*—Medium thickness; medium length.

*Stalk cavity.*—Medium depth; narrow width.

*Skin.*—Ribbing present but not prominent; slightly rough surface; bloom absent; greasiness absent; cracking tendency absent; medium to thicks skin; yellow-green ground colour; (10Y6/6).

*Over-colour.*—High percentage of overcolour; burgundy red; (5R3/6) solid flush; medium amount of russet around stalk.

*Lenticels.*—Medium size; prominent.

*Flesh.*—Firm; white (10Y8/3) fine texture; juicy; average flesh firmness at 1991 and 1992 harvest seasons were 8.60 and 9.80 kg-f, respectively; slow browning of flesh after cutting.

*Taste.*—Medium sweetness; medium acidity tangy flavor.

*Calyx tube.*—Short length; medium width; U or V shaped.

*Sinus.*—Closed.

*Aperture of locules.*—Closed when observed in cross-section.

*Central cavity.*—Present when observed in cross-section.

*Ripening.*—For eating, late; 8 days later than Granny Smith; harvest in Hastings in 1991 was between 11 April and 2 May; no water core has been discovered.

*Storage.*—Stores well physiologically for one hundred days at 0.5° C.

*Seed.*—Medium size; brown colour (10R2/3) when dry.

*Pest and disease.*—Some black spot.

What we claim is:

1. A new and distinct variety of apple tree substantially as herein described and illustrated characterised by a high percentage of burgundy red overcolour.

* * * * *